US 12,144,540 B2

(12) United States Patent
Tegg et al.

(10) Patent No.: US 12,144,540 B2
(45) Date of Patent: Nov. 19, 2024

(54) PULMONARY VEIN ISOLATION BALLOON CATHETER

(71) Applicant: St. Jude Medical, Cardiology Division, Inc., St. Paul, MN (US)

(72) Inventors: Troy T. Tegg, Elk River, MN (US); Salo Arias, Brooklyn Park, MN (US); Derek C. Sutermeister, Ham Lake, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 898 days.

(21) Appl. No.: 16/758,799

(22) PCT Filed: Oct. 26, 2018

(86) PCT No.: PCT/US2018/057767
§ 371 (c)(1),
(2) Date: Apr. 23, 2020

(87) PCT Pub. No.: WO2019/084442
PCT Pub. Date: May 2, 2019

(65) Prior Publication Data
US 2021/0177505 A1    Jun. 17, 2021

Related U.S. Application Data

(60) Provisional application No. 62/578,178, filed on Oct. 27, 2017.

(51) Int. Cl.
*A61B 18/24*    (2006.01)
*A61B 18/02*    (2006.01)
(Continued)

(52) U.S. Cl.
CPC ...... *A61B 18/1492* (2013.01); *A61B 18/0206* (2013.01); *A61B 18/24* (2013.01);
(Continued)

(58) Field of Classification Search
CPC . A61B 18/0206; A61B 18/1492; A61B 18/24; A61B 2018/0022;
(Continued)

(56) References Cited

U.S. PATENT DOCUMENTS 6,652,515 B1 * 11/2003 Maguire ................ A61N 7/02
606/49
8,382,689 B2    2/2013 Sliwa et al.
(Continued)

FOREIGN PATENT DOCUMENTS

| WO | 2019083764 A1 | 5/2019 |
| WO | 2019083765 A1 | 5/2019 |
| WO | 2019084439 A1 | 5/2019 |

*Primary Examiner* — Michael F Peffley
*Assistant Examiner* — Amanda L Zink
(74) *Attorney, Agent, or Firm* — Armstrong Teasdale LLP

(57) ABSTRACT

An elongate medical device having a device longitudinal axis and a device distal region, the medical device comprising a balloon at the device distal region and having a balloon longitudinal axis, the balloon comprising a balloon inflatable portion with a first length configured to transition from a deflated state to an inflated state and includes a portion of the balloon proximal portion and a portion of the balloon distal portion, a balloon proximal portion with a second length, a balloon distal portion with a third length, wherein, in the inflated state, the balloon is symmetrical about the balloon longitudinal axis and the balloon comprises a first profile shape with a second length and a second profile shape with a third length, and wherein the balloon distal portion comprising the second profile shape comprises a tissue contacting surface where a substantial portion of the tissue contacting surface is concave.

23 Claims, 6 Drawing Sheets

(51) Int. Cl.
*A61B 18/14* (2006.01)
*A61B 18/00* (2006.01)

(52) U.S. Cl.
CPC ............... *A61B 2018/00232* (2013.01); *A61B 2018/00375* (2013.01); *A61B 2018/00577* (2013.01); *A61B 2018/00613* (2013.01); *A61B 2018/0212* (2013.01); *A61B 2018/0262* (2013.01)

(58) Field of Classification Search
CPC ........... A61B 2018/00232; A61B 2018/00375; A61B 2018/00577; A61B 2018/00613; A61B 2018/0212; A61B 2018/0262
See application file for complete search history.

(56) References Cited

U.S. PATENT DOCUMENTS

| | | |
|---|---|---|
| 8,449,538 B2 | 5/2013 | Long |
| 8,728,073 B2* | 5/2014 | McDaniel .......... A61B 18/1492 606/41 |
| 8,790,341 B2 | 7/2014 | Pappone et al. |
| 9,289,606 B2 | 3/2016 | Paul et al. |
| 2002/0029062 A1* | 3/2002 | Satake ................. A61M 25/10 606/194 |
| 2004/0019349 A1* | 1/2004 | Fuimaono ........ A61B 17/22012 606/41 |
| 2005/0171525 A1* | 8/2005 | Rioux ................ A61B 18/1492 606/41 |
| 2005/0273095 A1* | 12/2005 | Taimisto ............ A61B 18/1492 606/41 |
| 2007/0255394 A1* | 11/2007 | Ryan .................... A61F 2/2418 623/1.24 |
| 2019/0343578 A1 | 11/2019 | Olson |
| 2020/0085483 A1 | 3/2020 | Tegg et al. |
| 2020/0085484 A1 | 3/2020 | Tegg et al. |
| 2023/0014644 A1* | 1/2023 | Salehzadeh Einabad .................. G02B 6/136 |

* cited by examiner

PULMONARY VEIN ISOLATION BALLOON CATHETER

CROSS-REFERENCE TO RELATED APPLICATIONS

This application claims the benefit of U.S. provisional application No. 62/578,178, filed 27 Oct. 2018, which is hereby incorporated by reference as though fully set forth herein.

BACKGROUND a. Field

The instant disclosure relates to catheters, in particular catheters for conducting diagnostics or ablation therapy within a heart. In one embodiment, the instant disclosure relates to a catheter for treating cardiac arrhythmias by ablating in the vicinity of pulmonary venous tissue.

b. Background Art

The human heart routinely experiences electrical currents traversing its many surfaces and ventricles, including the endocardial chamber. Just prior to each heart contraction, heart depolarizes and repolarizes, as electrical currents spread across the heart and throughout the body. In healthy hearts, the surfaces and ventricles of the heart will experience an orderly progression of depolarization waves. In unhealthy hearts, such as those experiencing atrial arrhythmia, including for example, ectopic atrial tachycardia, atrial fibrillation, and atrial flutter, the progression of the depolarization wave becomes chaotic. Arrhythmias may persist as a result of scar tissue or other obstacles to rapid and uniform depolarization. These obstacles may cause depolarization waves to electrically circulate through some parts of the heart more than once. Atrial arrhythmia can create a variety of dangerous conditions, including irregular heart rates, loss of synchronous atrioventricular contractions, and blood flow stasis. All of these conditions have been associated with a variety of ailments, including death.

Catheters are used in a variety of diagnostic and/or therapeutic medical procedures to correct conditions such as atrial arrhythmia, including for example, ectopic atrial tachycardia, atrial fibrillation, and atrial flutter.

Typically in a procedure, a catheter is manipulated through a patient's vasculature to, for example, a patient's heart, and carries one or more electrodes which may be used for mapping, ablation, diagnosis, or other treatments. Where an ablation therapy is desired to alleviate symptoms including atrial arrhythmia, an ablation catheter imparts ablative energy to cardiac tissue to create a lesion in the cardiac tissue. The lesioned tissue is less capable of conducting electrical signals, thereby disrupting undesirable electrical pathways and limiting or preventing stray electrical signals that lead to arrhythmias. The ablation catheter may utilize ablative energy including, for example, radio frequency (RF), cryoablation, laser, chemical, and high-intensity focused ultrasound.

The foregoing discussion is intended only to illustrate the present field and should not be taken as a disavowal of claim scope.

BRIEF SUMMARY

The instant disclosure relates to electrophysiology catheters for conducting diagnostics or tissue ablation within a heart. In particular, the instant disclosure relates to an electrophysiology catheter that either conforms to a shape of a pulmonary vein or deforms the tissue to the balloon shape for therapy of cardiac arrhythmias and produces a consistent tissue ablation line along a length and circumference of the pulmonary venous tissue.

Aspects of the present disclosure are directed to an elongate medical device having a device longitudinal axis and a device distal region, the medical device comprising a balloon at the device distal region and having a balloon longitudinal axis, the balloon comprising a balloon inflatable portion with a first length that is configured to transition from a deflated state to an inflated state and includes a portion of the balloon proximal portion and a portion of the balloon distal portion, a balloon proximal portion with a second length, a balloon distal portion with a third length, wherein, in the inflated state, the balloon is symmetrical about the balloon longitudinal axis and a plan view of the balloon comprises a first profile shape with a second length and a second profile shape with a third length, and wherein the balloon distal portion comprising the second profile shape comprises a tissue contacting surface where a substantial portion of the tissue contacting surface is concave.

In one exemplary embodiment of the present disclosure, a system for treating atrial fibrillation is taught. The system comprises a balloon delivery catheter including proximal and distal ends; and an ablation balloon comprising a first section, a second section, a third section, and an inflatable section that comprises the second section and a portion of the first section and a portion of the third section, where the ablation balloon is coupled to the distal end of the balloon delivery catheter, wherein the first section has a first profile shape, the third section with a second profile shape is a portion of the third section is configured to engage with an ostium of a pulmonary vein for aligning a longitudinal axis of the ablation balloon with a longitudinal axis of the pulmonary vein, and the second section couples the first and third sections of the ablation balloon, with a varying circumference, and wherein at least a portion of one of the second section and third section of the ablation balloon is configured, when the inflatable section is inflated, to engage with an antrum of the pulmonary vein along an uninterrupted length and circumference, and deliver a uniform ablation therapy to the pulmonary vein antrum.

In another embodiment of the present disclosure, a balloon catheter is disclosed for pulmonary vein isolation. The balloon catheter including a catheter shaft configured to deploy an ablation balloon into a pulmonary vein, the ablation balloon coupled to a distal end of the catheter shaft, and configured to deploy from an undeployed configuration to a deployed configuration having a concave tissue contacting surface, engage, by a portion the concave tissue contacting surface, a tissue wall of the pulmonary vein along an uninterrupted length and circumference of an antrum and ostia of the pulmonary vein, and wherein the ablation balloon is configured to deliver a uniform ablation therapy to the antrum of the pulmonary vein engaged by the portion of the concave tissue contacting surface of the ablation balloon.

In yet another embodiment of the present disclosure, an expandable medical device is disclosed for pulmonary vein isolation. The expandable medical device comprising a balloon that is configured to transition from a deflated state to an inflated state, wherein when the balloon is in the inflated state, the balloon comprises a first profile shape on a proximal portion and a second profile shape on a distal portion, where the balloon is configured to be coupled with an elongated medical device and the second profile shape is a concave shape.

The foregoing and other aspects, features, details, utilities, and advantages of the present disclosure will be apparent from reading the following description and claims, and from reviewing the accompanying drawings.

BRIEF DESCRIPTION OF THE DRAWINGS

Various example embodiments may be more completely understood in consideration of the following detailed description in connection with the accompanying drawings.

Figure 1:
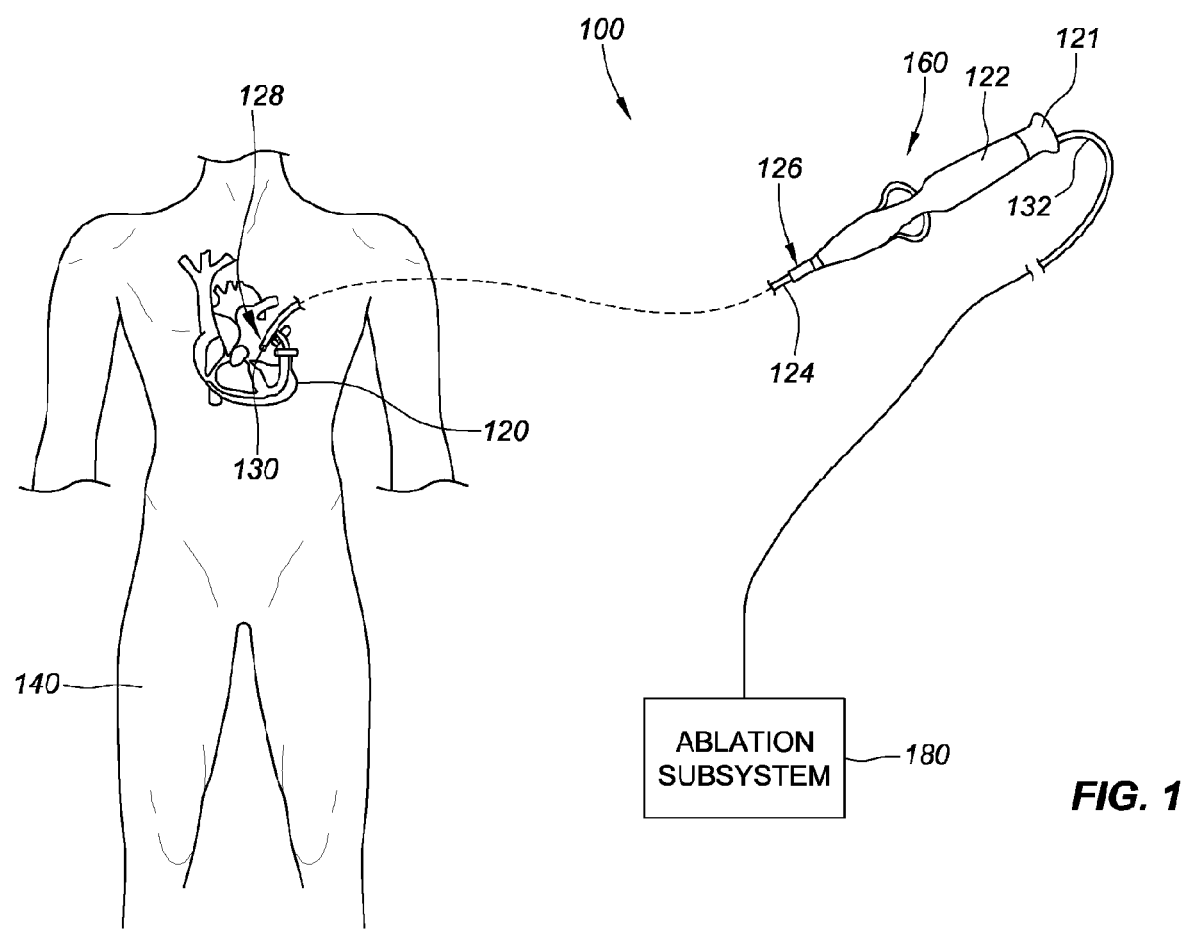
FIG. 1 is a schematic and diagrammatic view of a catheter system for performing a therapeutic medical procedure, consistent with various aspects of the present disclosure.

While various embodiments discussed herein are amenable to modifications and alternative forms, aspects thereof have been shown by way of example in the drawings and will be described in detail. It should be understood, however, that the intention is not to limit the scope to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION OF EMBODIMENTS

The instant disclosure relates to electrophysiology catheters for conducting diagnostics or tissue ablation within a heart. In particular, the instant disclosure relates to an electrophysiology catheter that either conforms to a shape of a pulmonary vein or deforms the tissue to the balloon shape for therapy of cardiac arrhythmias and produces a consistent tissue ablation line along a length and circumference of the pulmonary venous tissue. Details of the various embodiments of the present disclosure are described below with specific reference to the figures.

Typically, ablation therapies have been delivered by making a number of individual ablations in a controlled fashion in order to form a lesion line. Such lesion lines are often desirably formed around/between the pulmonary veins in the left atrium of the heart which have been associated with an introduction point of erratic electric signals into the heart. This type of ablation therapy requires precise positioning of the ablation catheter for optimal results. There are devices in development or being commercialized that attempt to achieve a sufficient block of ablations with minimal applications of energy. Existing designs range from diagnostic catheters with hoop and balloon mounted designs with energy applying features. Existing designs suffer from a lack of continuous contact around a circumference and length of the pulmonary vein during therapy deliver, resulting in inconsistent lesion lines and incomplete electrical signal blockage.

Referring now to the drawings wherein like reference numerals are used to identify similar components in the various views, FIG. 1 is a schematic and diagrammatic view of a catheter ablation system 100 for performing a tissue ablation procedure. In an exemplary embodiment, tissue 120 (e.g., cardiac tissue, and heart) comprises cardiac tissue within a human body 140. It should be understood, however, that the system may find application in connection with a variety of other tissues within human and non-human bodies, and therefore, the present disclosure is not meant to be limited to the use of the system in connection with only cardiac tissue and/or human bodies.

Catheter ablation system 100 may include a catheter 160 and an ablation subsystem 180 for controlling an ablation therapy conducted by an ablation balloon 130 at a distal end of the catheter 160. The ablation subsystem 180 can control the application of and/or generation of ablative energy including, for example, radio frequency (RF), direct current (DC), irreversible electroporation, cryoablation, laser, chemical, and high-intensity focused ultrasound. Example embodiments of such ablation subsystems are described in U.S. Pat. Nos. 8,449,538, 9,289,606, 8,382,689, and 8,790,341, which are hereby incorporated by reference as though fully set forth herein.

In the exemplary embodiment of FIG. 1, catheter 160 is provided for examination, diagnosis, and/or treatment of internal body tissue such as cardiac tissue 120. The catheter may include a cable connector or interface 121, a handle 122, a shaft 124 having a proximal end 126 and a distal end 128 (as used herein, "proximal" refers to a direction toward the end of the catheter 160 near the handle 122, and "distal" refers to a direction away from the handle 122), and an ablation balloon 130 coupled to the distal end of the catheter shaft 124.

In an exemplary embodiment, ablation balloon 130 is manipulated through vasculature of a patient 140 using handle 122 to steer one or more portions of shaft 124 and position the ablation balloon at a desired location within heart 120. In various embodiments, the ablation balloon includes ablation elements (e.g., ablation electrodes, high intensity focused ultrasound ablation elements, etc.) that when operated by ablation subsystem 180 ablates the tissue 120 in contact with the ablation balloon 130 (and in some cases tissue 120 in proximity to the ablation balloon 130 may be ablated by conductive energy transfer through the blood pool and to the proximal tissue).

In various specific embodiments of the present disclosure, catheter 160 may include electrodes and one or more positioning sensors at a distal end 128 of catheter shaft 124 (e.g., electrodes or magnetic sensors). In such an embodiment, the electrodes acquire EP data relating to cardiac tissue 120, while the positioning sensor(s) generate positioning data indicative of the 3-D position of the ablation balloon 130. In further embodiments, the catheter 160 may further include other conventional catheter components such as, for example and without limitation, steering wires and actuators, irrigation lumens and ports, pressure sensors, contact sensors, temperature sensors, additional electrodes, and corresponding conductors or leads.

Connector 121 provides mechanical and electrical connection(s) for one or more cables 132 extending, for example, from ablation subsystem 180 to ablation balloon 130 mounted on, along, within, or through the distal end 128 of catheter shaft 124. In other embodiments, the connector may also provide mechanical, electrical, and/or fluid connections for cables extending from other components in catheter system 100, such as, for example, a fluid source (when the catheter 160 comprises an irrigated catheter) and contact/pressure sensing circuitry. The connector 121 is conventional in the art and is disposed at a proximal end 126 of the catheter 160.

Handle 122 provides a location for a user to hold catheter 160 and may further provide steering or guidance for the shaft 124 within the body 140. For example, the handle 122 may include means to manipulate one or more steering wires extending through the catheter 160 to a distal end 128 of the shaft 124 to steer the shaft. The handle 122 is conventional in the art and it will be understood that the construction of the handle may vary. In other embodiments, control of the catheter 160 may be automated by robotically driving or controlling the catheter shaft 124, or driving and controlling the catheter shaft 124 using a magnetic-based guidance system.

Catheter shaft 124 is an elongated, tubular, and flexible member configured for movement within a patient's body 140. The shaft supports an ablation balloon 130 at a distal end 128 of catheter 160. The shaft 124 may also permit transport, delivery and/or removal of fluids (including irrigation fluids, cryogenic ablation fluids, and body fluids), medicines, and/or surgical tools or instruments. The shaft 124, which may be made from conventional materials used for catheters, such as PEBAX or polyurethane, defines one or more lumens configured to house and/or transport electrical conductors, fluids, and/or surgical tools. The catheter may be introduced into a blood vessel or other structure within the body 140 through a conventional introducer sheath.

In an exemplary cardiac ablation therapy, to correct for atrial arrhythmia, the introducer sheath is introduced through a peripheral vein (typically a femoral vein) and advanced into the right atrium, in what is referred to as a transeptal approach. The introducer sheath is then used to make an incision in the fossa ovalis (the tissue wall between the left and right atriums), and extends through the incision in the fossa ovalis to anchor the introducer sheath in the fossa ovalis. The ablation catheter 160 may then be extended through a lumen of the introducer sheath into the left atrium. Catheter shaft 124 of ablation catheter 160 may then be steered or guided through the left atrium to position an ablation balloon 130 into a desired location within the left atrium such as a pulmonary vein.

During cardiac ablation therapy, it is desirable to align the centerline of ablation balloon 130 with a centerline of a pulmonary vein in which the ablation therapy is to take place. Alignment of the ablation balloon is particularly difficult in many embodiments due to the transeptal approach through the fossa ovalis which causes the shaft 124 to be naturally biased toward a left side of a patient's body 140. This bias places an additional torque on ablation catheter system 100, which may result in the ablation balloon, after placement within the pulmonary vein, to bias away from the centerline of the pulmonary vein. Where the ablation balloon 130 is deployed away from the centerline of the pulmonary vein, the deployment may result in uneven contact pressure and corresponding uneven pulmonary vein tissue wall stress. It has been discovered that contact area and tissue strain are associated with decreased ablation therapy efficacy. Aspects of the present disclosure improve the efficacy of ablation therapy by more effectively positioning the ablation balloon 130 circumferential with a centerline of the pulmonary vein. In more specific embodiments, the deployed ablation balloon 130 further improves ablation therapy efficacy by having improved contour mapping to the pulmonary vein, thereby deploying and engaging the pulmonary vein along an extended and uninterrupted length and circumference of the ablation balloon 130.

Figure 2:
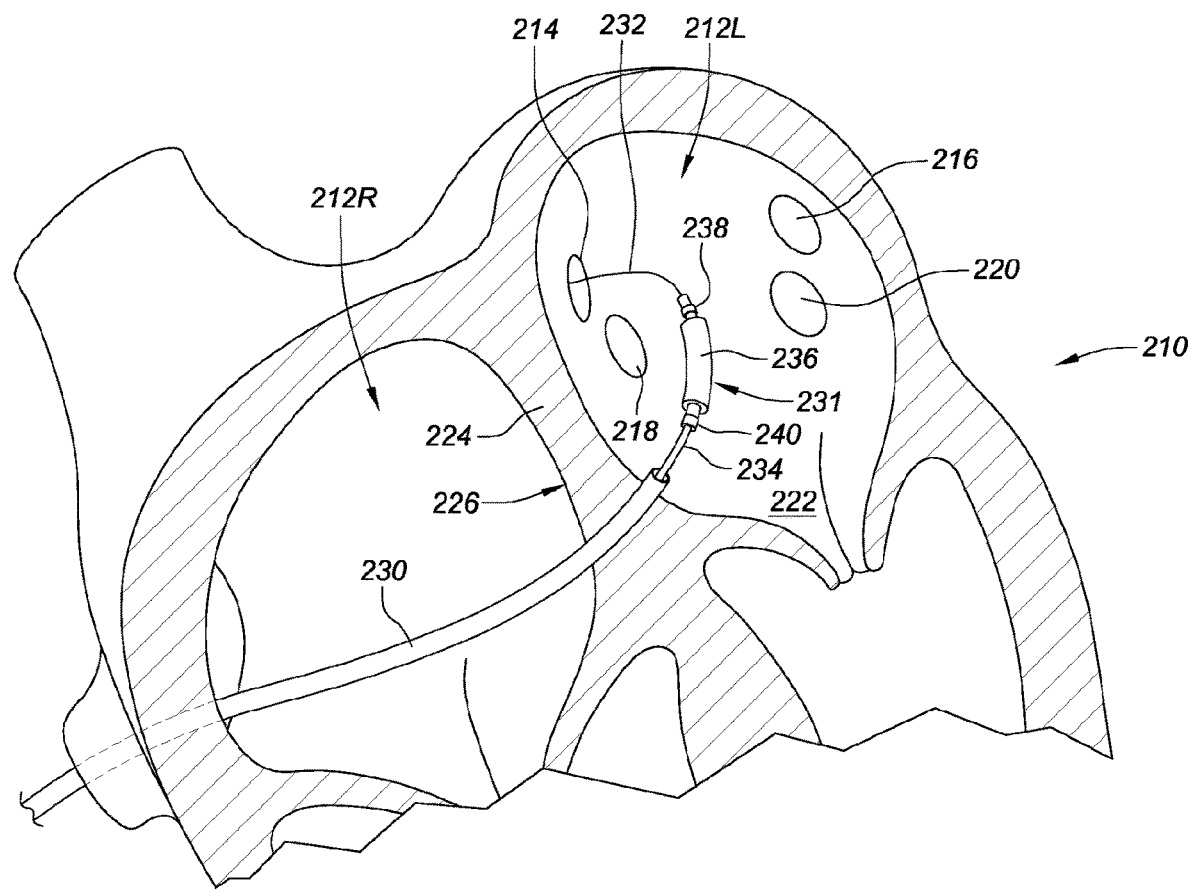
FIG. 2 is a cross-sectional front-view of a portion of a heart with an ablation balloon catheter locating a pulmonary vein from within the left atrium, consistent with various aspects of the present disclosure.

FIG. 2 is a cross-sectional front-view of a portion of a heart 210 with an ablation balloon catheter 231 in a deflated state locating a pulmonary vein (e.g., 214, 216, 218, and 220) from within left atrium 212L, consistent with various aspects of the present disclosure. Such an approach may be used for performing atrial fibrillation therapy. As shown in FIG. 2, the cardiac muscle 210 includes two upper chambers called the left atrium 212L and right atrium 212R, and two lower chambers called the left ventricle and right ventricle (not shown).

Aspects of the present disclosure are directed to ablation therapies in which tissue in pulmonary veins 214, 216, 218, and 220, which form conductive pathways for electrical signals traveling through the tissue, is destroyed in order to electrically isolate sources of unwanted electrical impulses (arrhythmiatic foci) located in or near the pulmonary veins. By either destroying the arrhythmiatic foci, or electrically isolating them from the left atrium 212L, the cause of atrial fibrillation can be reduced or eliminated.

As shown in FIG. 2, an ablation balloon catheter 231 may be introduced into the left atrium 212L by an introducer sheath 230. A guidewire and a steerable portion of the catheter shaft, 232 and 234, respectively, may guide the ablation balloon 236 once introduced into the left atrium 212L by the introducer sheath 230. Optionally, the ablation balloon catheter 231 may include mapping electrodes at proximal and distal ends of ablation balloon, 240 and 238, respectively. In operation, introducer sheath 230 has its distal end positioned within left atrium 212L. As shown in FIG. 2, a transeptal approach may be utilized in which introducer sheath 230 is introduced through a peripheral vein (typically a femoral vein) and advanced to right atrium 212R. The introducer sheath 230 is used to make a small incision into the fossa ovalis 226 which allows the distal end of the introducer sheath 230 to enter the left atrium 212L (through the transeptal wall 224) and to anchor itself to the wall of the fossa ovalis 226.

Ablation balloon catheter 234 may also be introduced into left atrium 212L through the arterial system. In that case, introducer sheath 230 is introduced into an artery (such as a femoral artery) and advanced retrograde through the artery to the aorta, the aortic arch, and into the left ventricle. The ablation balloon catheter 234 is then extended from within a lumen of the introducer sheath 230 to enter the left atrium 212L through mitral valve 222.

Once introducer sheath 230 is in position within left atrium 212L, steerable ablation balloon catheter 231 is advanced out a distal end of the introducer sheath and toward one of the pulmonary veins (e.g., 214, 216, 218, and 220). In FIG. 2, the target pulmonary vein is right superior pulmonary vein 214. A guidewire 232 and a steerable portion 234 of the ablation balloon catheter are manipulated until the distal tip of the ablation balloon catheter is directed toward the ostium of the target pulmonary vein, after which the ablation balloon is extended toward the pulmonary vein (e.g., superior pulmonary vein 214).

Carried near a distal end of ablation balloon catheter 231, ablation balloon 236 remains in a collapsed condition so that it may pass through introducer sheath 230, and approach the target pulmonary vein 214. Once in proximity, the ablation balloon 236 is deployed, so that it may be advanced to engage and secure the ablation balloon catheter 231 in a position axial to the target pulmonary vein 214.

As optionally shown, the embodiment of FIG. 2 may include mapping electrodes 238 and 240. The mapping electrodes 238 and 240 may be ring electrodes that allow the clinician to perform a pre-deployment electrical mapping of the conduction potentials of the pulmonary vein 214. Although shown as being carried on ablation balloon catheter 231, mapping electrodes may alternatively be carried on-board a separate electrophysiology catheter.

To ablate the tissue, once deployed, ablation balloon 236 may electrically conduct a DC energy current into the targeted tissue of the pulmonary vein 214. In other embodiments, the ablation balloon 236 may transmit radio-frequency energy to ablate the target tissue. In yet other embodiments, the ablation balloon 236 may deliver one or more of the following energies to the targeted tissue: cryoablation, laser, chemical, and high-intensity focused ultrasound, among others.

Figure 3:
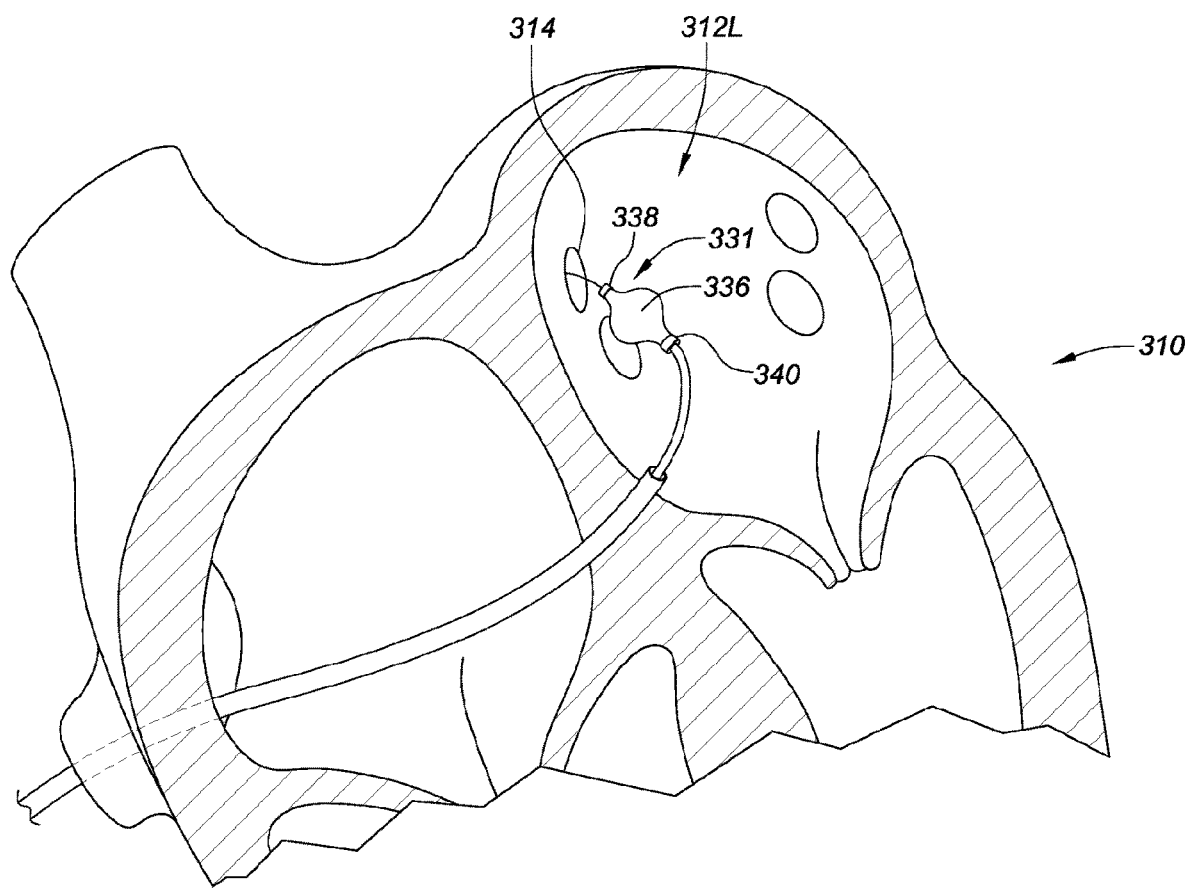
FIG. 3 is a cross-sectional front-view of a left atrium with an ablation balloon catheter where the ablation balloon is inflated prior to contact with tissue proximate a pulmonary vein, consistent with various aspects of the present disclosure.

FIG. 3 shows an ablation balloon catheter 331 including an ablation balloon 336 in an inflated state prior to contact with tissue proximate a pulmonary vein 314. After inflation, the distal end of the ablation balloon catheter 331 enters the pulmonary vein 314, mapping may be conducted using electrodes 338 and/or 340 in order to verify proper location prior to deployment of the ablation balloon 336.

It has been discovered that proper positioning of the ablation balloon within the pulmonary vein is critical to the efficacy of an ablation therapy. For example, if the ablation balloon is not centered axially within the pulmonary vein when inflated, a portion of the ablation balloon may not contact a portion of the pulmonary vein circumference. This portion of non-lesioned tissue will allow for the continued conduction of electrical signals through the pulmonary vein and into the left atrium 312L of the heart 310. Such non-lesioned tissue greatly impedes the efficacy of the lesioned tissue to limit the flow of stray electrical signals that cause arrhythmias. Moreover, the ill-centered position and uneven pressure of the ablation balloon within the pulmonary vein 314 may overly-stress pulmonary vein tissue that is in contact with the ablation balloon 336 when inflated, and may also reposition the pulmonary vein closer to structures (e.g., phrenic and esophageal nerves) that can be damaged by a nominal lesion depth of the ablation therapy. The Applicant has discovered that overly-straining the pulmonary vein tissue results in thin tissue and a deeper lesion than desired; similarly, under-straining the pulmonary vein tissue results in thicker tissue a shallower lesion than desired—all of which decreases ablation therapy efficacy. Specifically, stressed tissue is less likely to evenly ablate and may even exhibit increased thermal capacity capability, therefore being capable of absorbing increased ablation energy before necrosis. Accordingly, aspects of the present disclosure improve the fit of the ablation balloon 336 at the ostium of the pulmonary vein 314 with an ablation balloon profile that better conforms to the contours of the pulmonary vein 314. This improved conformance between the inflated ablation balloon 336 and pulmonary vein 314 results in improved ablation therapy efficacy, and the reduced need for duplicative therapies.

Figure 4:
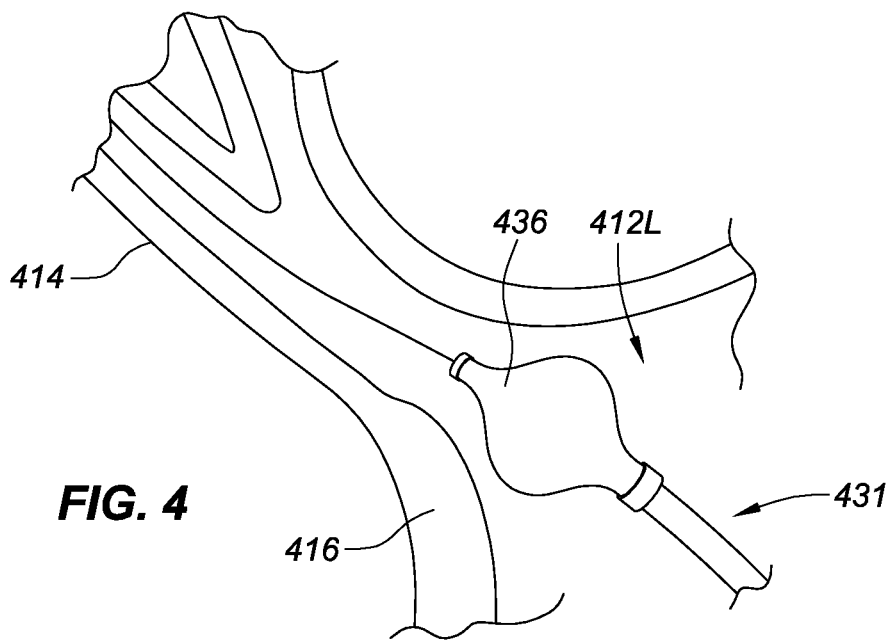
FIG. 4 is a cross-sectional front-view of portions of a left atrium and a pulmonary vein with an ablation balloon catheter positioned therein, prior to deployment of the ablation balloon, consistent with various aspects of the present disclosure.

FIG. 4 is a cross-sectional front-view of portions of a left atrium 412L and a pulmonary vein 414 with an ablation balloon catheter 431 positioned therein, after deployment of the ablation balloon 436 (e.g., in an inflated state), consistent with various aspects of the present disclosure. As shown in FIG. 4, the ablation balloon 436 is proximate the pulmonary vein 414 prior to balloon deployment and proximate an antral portion 416 of the target pulmonary vein 414. In one embodiment of the present disclosure, the proper location of the ablation balloon may be determined/verified by mapping, prior to deployment of the ablation balloon.

Figure 5:
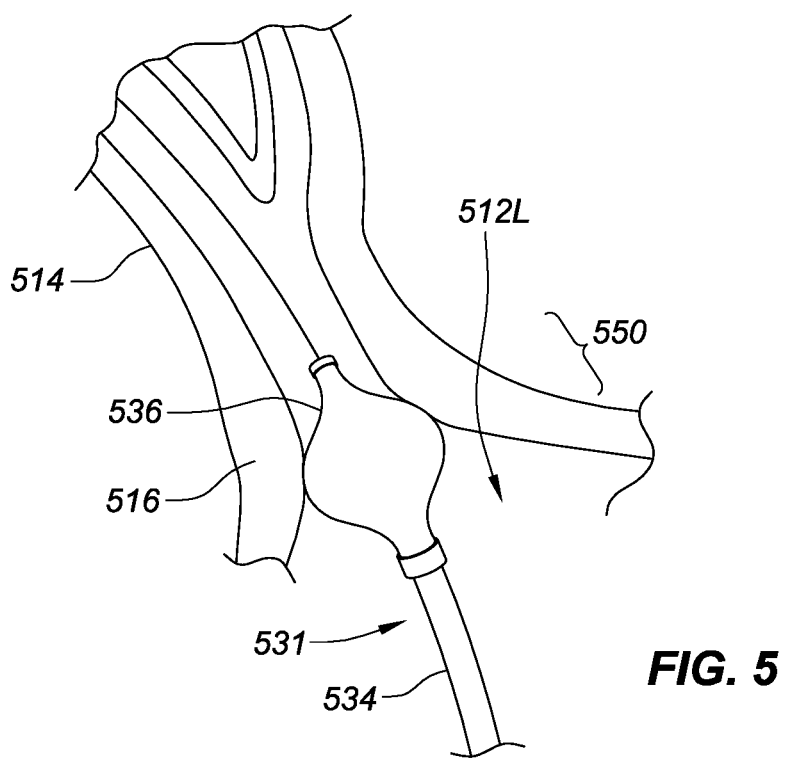
FIG. 5 is a cross-sectional front-view of a pulmonary vein with an ablation balloon catheter deployed therein, consistent with various aspects of the present disclosure.

FIG. 5 shows expanded ablation balloon 536 (e.g., an inflated state) engaged proximate the antral portion 516 of target pulmonary vein 514. The ablation balloon 536 can have various shapes when expanded/inflated, as further discussed in relation to FIGS. 6-10. The various shapes can be designed to, for example, more precisely match the contours of the pulmonary vein, reduce the chance of perforation of tissue before, during, and after a procedure with the ablation balloon.

This ablation balloon shape shown in FIG. 5 can increase the surface area contact between tissue proximate the pulmonary vein and the expanded/inflated ablation balloon, which consequently improves the efficacy of the ablation therapy that relies on surface contact between the ablation balloon and tissue proximate the pulmonary vein tissue. Without continuous contact along a circumference of tissue proximate of the pulmonary vein, a continuous lesion along the circumference may not be formed. As a result, stray electrical signals (though likely decreased in strength) may still be able to travel between the pulmonary vein and left atrium 512L. Accordingly, the patient may still experience cardiac arrhythmias. As such, continuous contact along a diameter of the tissue proximate the pulmonary vein is necessary to completely ablate the tissue proximate the pulmonary vein tissue and to mitigate all electrical signal communication between the pulmonary vein and the left atrium. To achieve such continuous contact, the present disclosure teaches a multi-contour ablation balloon with at least three distinct portions for more effective ablation therapies.

In its expanded/inflated state shown in FIG. 5, ablation balloon 536 engages tissue proximate pulmonary vein 514. Through one or more ablation processes mentioned above, the ablation balloon 536 produces a circumferential zone of ablation 550 along the tissue proximate the pulmonary vein proximate the antral 516 portion. The ablation zone electrically isolates the target pulmonary vein from left atrium 512L. To the extent that arrhythmiatic foci were located within the ablation zone, the arrhythmiatic foci are destroyed. To the extent the arrhythmiatic foci are located in the target pulmonary vein on the opposite side of the ablation zone from the left atrium, the electrical impulses produced by those foci are blocked or inhibited by the ablation zone.

In a typical ablation therapy, pulmonary veins are treated in accordance to their likelihood of having an arrhythmiatic foci. Often, all pulmonary veins are treated. The processes as described for right superior pulmonary vein 214 are similar for each of the three other pulmonary veins 216, 218, and 220 (see FIG. 2).

Once ablation therapy is complete, ablation balloon 536 may be deflated and ablation balloon catheter 534 may be retracted back into introducer sheath 230 (as shown in FIG. 2). An electrophysiology catheter, or sub-electrodes (e.g., 238 and 240 in FIG. 2) proximal and distal to the ablation balloon, may be used to verify the efficacy of the therapy prior to removal of the ablation balloon catheter 534. In various embodiments of the present disclosure, additional subelectrodes may also be positioned on a surface of the ablation balloon 536, either alone, or in conjunction with the subelectrodes 238 and 240.

Ablation balloons have been developed for a variety of different applications and take a number of different forms. Aspects of the present disclosure may utilize ablation balloons of various types and different mechanical construction. The ablation balloons may be either of a conductive or a nonconductive material and can be either self-erecting or mechanically erected, such as through the use of an internal balloon. In one example embodiment, a lumen extending through a length of a shaft of the ablation balloon catheter 534 may inject a fluid into the ablation balloon which exerts a radial force on the ablation balloon and thereby expands/inflates the balloon into an erect configuration (as shown in FIG. 5). The ablation balloons can be made from various polymers including, for example, PET, nylon, PEBAX, Pellethane® or Tecothane™. In some embodiments with multiple balloons, a lubricant can be included to facilitate expansion of the ablation balloons (e.g., less friction for the ablation balloons during deployment/retraction from an introducer (e.g., introducer 330 of FIG. 3)).

In certain specific embodiments, an ablation balloon may consist of non-compliant material (e.g., inflates to one specific size or size range, even as internal pressure increases). In such embodiments, over-expansion of a distal portion of the balloon near a portion of the pulmonary vein tissue wall may be prevented where the proximal portion of the balloon has come into contact with an antral portion (e.g. antral portion 516) of the pulmonary vein tissue wall. In other embodiments, the ablation balloon may consist of compliant material (expands as internal pressure increases) or a combination of compliant and non-compliant (e.g., one or more non-compliant portions of a balloon).

Figure 6:
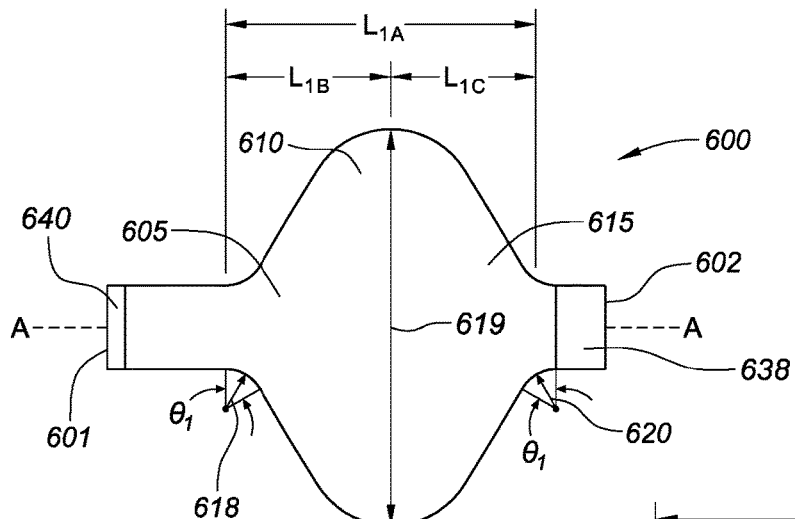
FIG. 6 is a plan view of an ablation balloon, consistent with various aspects of the present disclosure.

FIG. 6 is a plan view of an ablation balloon, consistent with various aspects of the present disclosure. An ablation balloon 600 can have a proximal end 601 with an electrode 640 and a distal end 602 with an electrode 638. The ablation balloon 600 can have a balloon longitudinal axis defined by the line A-A. The ablation balloon can be coupled with a distal region of a shaft (e.g., the shaft 124 of FIG. 1) that has a shaft longitudinal axis. The shaft can couple with the ablation balloon at, for example, an internal balloon distal surface and an internal balloon proximal surface (e.g., the balloon 600 can be coupled with the shaft at two locations such as the internal balloon distal surface and the internal balloon proximal surface) or a proximal end 601 of the ablation balloon 600. The ablation balloon 600 can have an inflatable portion with a length $L_{1A}$, where the length $L_{1A}$ is from a first location proximate a proximal end 601 to a second location proximate a distal end 602 of the ablation balloon 600. The length $L_{1A}$ can range from approximately 10 to 60 mm.

The ablation balloon 600 can include a first portion 605 (i.e., a proximal portion; a balloon proximal portion), a second portion 610, and a third portion 615 (i.e., a distal portion; a balloon distal portion). The proximal portion 605 can include a first profile radius 618 and can include, for example, a portion of the balloon 600 defined by a length $L_{1B}$. The second portion 610 can include a balloon waist 619 (e.g., a widest diameter of the balloon) that separates the proximal portion 605 and the distal portion 615 and can be designed to occlude an opening in a body (e.g., a pulmonary vein) and mate with an antral portion of the pulmonary vein. The distal portion 615 can be defined by a length $L_{1C}$ and can be designed to occlude an opening in a body (e.g., a pulmonary vein) and to mate with an ostial portion of the pulmonary vein. The distal portion 615 can be considered a tissue contacting surface as a portion can be in contact with tissue when inserted into/proximate the pulmonary vein. The distal portion 615 can include a radius 620 (e.g., a second profile radius) for the ablation balloon 600. The second profile radius 620 can, for example, range from 1 to 5 mm. By including the second portion 610 and/or the distal portion 615 with the second profile radius 620, the ablation balloon 600 is suited to conform to/with the contours of the pulmonary vein. In the embodiment shown in FIG. 6, the second profile radius 620 of the distal portion 615 of the ablation balloon 600 can allow for a better fit for some pulmonary vein profiles and can improve therapy delivery and long-term efficacy.

As shown in FIG. 6, the ablation balloon 600 can have a symmetrical shape. For example, the inflatable portion of the ablation balloon 600 can be symmetrical about the balloon longitudinal axis (defined by the line A-A) and/or the second profile radius 620 can be the same as the first profile radius 618 for the proximal portion 605 and the distal portion 615 and the length $L_{1B}$ can be one half of the length $L_{1A}$). The ablation balloon can be, at times, considered asymmetrical with respect to the proximal portion and distal portions (e.g., the second profile radius 620 can be different from the first profile radius 618 and the length $L_{1B}$ can be less than one half of the length $L_{1A}$ and the length $L_{1C}$ can be more than one half of the length $L_{1A}$; see FIGS. 7-9B and related discussion).

A size of the proximal portion 605 that includes a certain profile radius (e.g., the first profile radius 618) and can also be indicated by an angular measurement shown by an angle $\theta_1$ in FIG. 6. A size of the distal portion 615 can be the same angular measurement, $\theta_1$, for the second profile radius 620. In some embodiments, the balloon can include multiple different profile radii in the same portion (e.g., in the proximal portion 605 and/or the distal portion 615) and angular measurements can be used to describe the amount of the portion allocated to a particular profile radius and/or the location of that profile radius on the ablation balloon 600.s In one exemplary application of ablation balloon 600 of FIG. 6, the shape of the ablation balloon 600 may be tailor fit for a specific patient based on measurements (e.g., ultrasonic images, magnetic resonance images, etc.) of the patient's pulmonary vein and entrance thereto. Specifically, based on the measurements of the patient, a shape along the longitudinal axis of the ablation balloon 600 may be selected that mimics the shape of a portion of the pulmonary vein (and in some embodiments may vary along a length of the longitudinal axis).

In various embodiments of the present disclosure, an ablation balloon 600 is capable of conducting ablation therapy at more than one location of the ablation balloon. For example, energy can be delivered to the proximal portion 605, the second portion 610, and the distal portion 615 of the ablation balloon 600. In some embodiments, the second portion 610, the distal portion 615, or a combination thereof may simultaneously conduct ablation therapy. For example, ablation energy can be applied in series (or in parallel) to the second portion 610 and the distal portion 615.

In more specific embodiments, the amount of ablation therapy (e.g., energy transmitted to the tissue, and the length of therapy) conducted at a tissue location may be controlled individually.

In cryoablation specific applications of an ablation balloon catheter, a distal portion of the expanded ablation balloon centers the ablation balloon within and/or proximate a pulmonary vein and anchors it thereto. A second portion and a distal portion are then cooled to deliver a cryoablation therapy to an antral portion of the pulmonary vein. Once the ablation therapy is complete, the ablation balloon is deflated and the ablation balloon is removed from the pulmonary vein.

Figure 7:
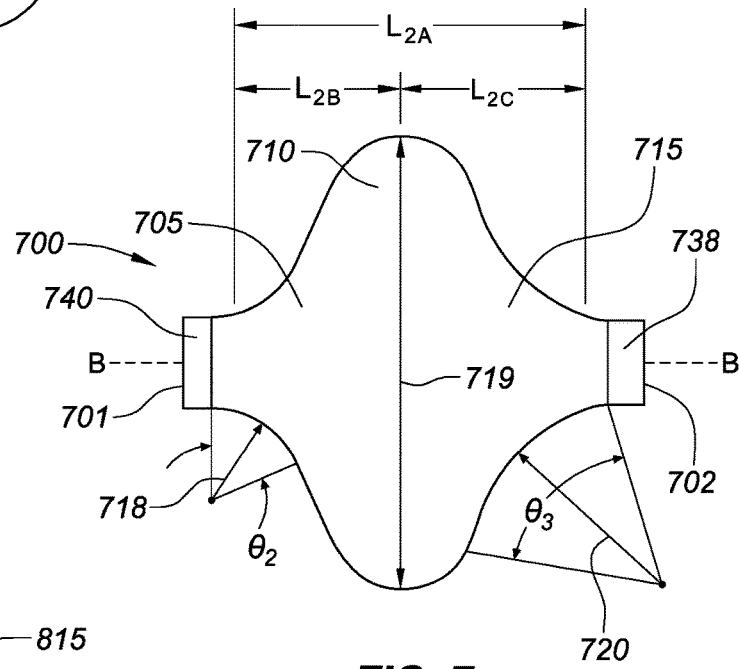
FIG. 7 is a plan view of an ablation balloon, consistent with various aspects of the present disclosure.

FIG. 7 is a plan view of an ablation balloon, consistent with various aspects of the present disclosure. The ablation balloon 700 can include a first portion 705 (i.e., a proximal portion; a balloon proximal portion), a second portion 710, and a third portion 715 (i.e., a distal portion; a balloon distal portion). The second portion 710 can include a balloon waist 719 (e.g., a widest diameter of the balloon) that separates the proximal portion 705 and the third portion 715. The ablation balloon 700 can have a balloon longitudinal axis defined by the line B-B. The ablation balloon 700 can have a proximal end 701 with an electrode 740 and a distal end 702 with an electrode 738 and can be coupled with a shaft (e.g., the shaft 124 of FIG. 1) at, for example, an internal balloon distal surface and an internal balloon proximal surface (e.g., the balloon 700 can be coupled with the shaft at two locations such as the internal balloon distal surface and the internal balloon proximal surface) or a proximal end 701 of the ablation balloon 700. The proximal portion 705 can include a first profile radius 718 and can include, for example, include a portion of the balloon 700 defined by a length $L_{2B}$. The second portion 710 can couple the proximal portion 705 and the distal portion 715 defined by a length $L_{2C}$ and can be designed to occlude an opening in a body (e.g., a pulmonary vein) and mate with an antral portion of the pulmonary vein. The distal portion 715 can be considered a tissue contacting surface as a portion can be in contact with tissue when inserted into/proximate the pulmonary vein. The distal portion 715 can include a radius 720 (e.g., a second profile radius) for a profile of a surface of the ablation balloon 700 (compared to the ablation balloon of FIG. 6). The second profile radius 720 can, for example, range from 10 mm to 30 mm.

The second profile radius 720, larger than the second profile radius 620 in FIG. 6, can, for example, allow for better axial alignment of the ablation balloon 700 within the pulmonary vein and can also provide for a better fit (e.g., increased contact area) between the ablation balloon 700 and adjacent tissue for some pulmonary vein profiles. The improved fit of the ablation balloon 700 with the pulmonary vein can allow for a better seal between the ablation balloon 700 and the pulmonary vein, which can allow for improved therapy (e.g., minimizing blood flow bypassing the ablation balloon during therapy and better contact between the ablation balloon 700 and the pulmonary vein). The ablation balloon 700 can have an inflatable portion with a length $L_{2A}$, where the length $L_{2A}$ is from a first location proximate a proximal end 701 to a second location proximate a distal end 702 of the ablation balloon 700. The inflatable portion can comprise a portion of the proximal portion 705 and a portion of the distal portion 715. The length $L_{2A}$ can range from 10 to 60 mm. The length $L_{2B}$ can be, in some embodiments, one half of the length $L_{2A}$. Other embodiments can have the length $L_{2B}$ as more or less than one half of the length $L_{2A}$.

As shown in FIG. 7, the ablation balloon 700 can have a symmetrical shape. For example, the inflatable portion of the ablation balloon 700 can be symmetrical about the balloon longitudinal axis defined by the line B-B. The ablation balloon 700 can be asymmetrical in shape with respect to the proximal portion 705 and the distal portion 715. For example, the ablation balloon 700 can have a concave profile in the proximal portion 705 and/or the distal portion 715, The concave profiles at the proximal portion 705 and the distal portion 715 can be the same or they can be different (as shown in FIG. 7). Other profiles for the proximal portion 705 and the distal portion 715 are also possible (e.g., linear, curved, convex, combinations of linear/curved/convex/concave, etc.) including combinations of profiles in a single portion (e.g., the proximal portion 705 can include a linear portion, a first concave portion, and a second concave portion, etc.). The shapes of the proximal portion 705 and the distal portion 715 can be described as polynomial expressions, where the polynomial expressions can be at least a second degree polynomial. In some embodiments, the second profile radius 720 can be different from the first profile radius 718 for the proximal portion 705 and the length $L_{2B}$ can be more or less than one half of the length $L_{2A}$.

A size of the proximal portion 705 that includes a certain profile radius (e.g., the first profile radius 718) can be indicated by an angular measurement shown by an angle $\theta_2$ in FIG. 7. A size of the distal portion 715 can be a different angular measurement, $\theta_3$, for the second profile radius 720. In some embodiments, the balloon can include multiple different profile radii in the same portion (e.g., in the proximal portion 705 and/or the distal portion 715) and angular measurements can be used to describe the amount of the portion allocated to a particular profile radius and/or the location of that profile radius on the ablation balloon 700.

Figure 8:
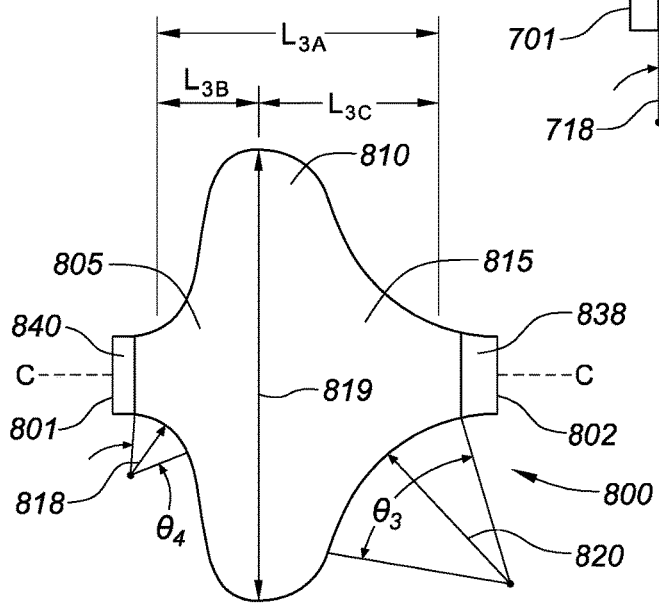
FIG. 8 is a plan view of an ablation balloon, consistent with various aspects of the present disclosure.

FIG. 8 is a plan view of an ablation balloon, consistent with various aspects of the present disclosure. The ablation balloon 800 can have a proximal end 801 with an electrode 840 and a distal end 802 with an electrode 838 and can be coupled with a shaft (e.g., the shaft 124 of FIG. 1) at, for example, an internal balloon distal surface and an internal balloon proximal surface (e.g., the balloon 800 can be coupled with the shaft at two locations such as the internal balloon distal surface and the internal balloon proximal surface) or a proximal end 801 of the ablation balloon 800. The ablation balloon 800 can include a first portion 805 (i.e., a proximal portion; a balloon proximal portion), a second portion 810, and a third portion 815 (i.e., a. The second portion 810 can include a balloon waist 819 (e.g., a widest diameter of the balloon) that separates the first portion 805 and the third portion 815 (i.e., a distal portion; a balloon distal portion). The first portion 805 can include a portion of the balloon 800 defined by a length $L_{3B}$. The second portion 810 can couple to the first portion 805 and the third portion 815 and can be designed to occlude an opening in a body (e.g., a pulmonary vein) and mate with an antral portion of the pulmonary vein. The distal portion 815 can be considered a tissue contacting surface as a portion can be in contact with tissue when inserted into/proximate the pulmonary vein. The third portion 815 can include a radius 820 (e.g., a second profile radius) for a different profile of a surface of the ablation balloon 800 (compared to the ablation balloon of FIGS. 6-7) for fitting with various pulmonary vein shapes. The second profile radius 820 can range from 10 to 30 mm.

The ablation balloon 800 can have an inflatable portion with a length $L_{3A}$, where the length $L_{3A}$ is from a first location proximate a proximal end 801 to a second location proximate a distal end 802 of the ablation balloon 800. The inflatable portion can comprise a portion of the proximal portion 805 and a portion of the distal portion 815. The length $L_{3A}$ can range from 10 to 60 mm. Length $L_{3A}$ can be shorter than $L_{2A}$ or $L_{1A}$ of FIGS. 6-7 respectively, which allows the ablation balloon 800 shown in FIG. 8 to be more maneuverable (compared to the ablation balloons 600 and 700 of FIGS. 6-7). The increased maneuverability can, for example, allow for easier/more effective placement of the ablation balloon 800 and can also reduce the risk of damage (e.g., perforation) to tissue during placement and/or movement of the ablation balloon 800. The length $L_{3B}$ can be minimized (e.g., using selected profile shapes) to help minimize the overall length $L_{3A}$ to maximize the maneuverability of the ablation balloon 800. The length $L_{3B}$ can be, in some embodiments, less than half the length $L_{3A}$. For example, $L_{3B}$ can be 10%, 20%, 25%, 30%, 33%, 40%, 45%, or any other suitable portion of $L_{3A}$ that is less than 50%.

As shown in FIG. 8, the ablation balloon 800 can have a symmetrical shape. For example, the inflatable portion of the ablation balloon 800 can be symmetrical about the balloon longitudinal axis (defined by the line C-C). The ablation balloon 800 can be asymmetrical in shape with respect to the proximal portion and the distal portion. For example, the ablation balloon 800 can have a concave profile in the first portion 805 and/or the third portion 815. Other profiles for the first portion 805 and the third portion 815 are also possible (e.g., linear, curved, convex, combinations of linear/curved/convex/concave, etc.) including combinations of profiles in a single portion (e.g., the first portion 805 can include a linear portion, a first concave portion, and a second concave portion, etc.). The shapes of the proximal portion 805 and the distal portion 815 can be described as polynomial expressions, where the polynomial expressions can be at least a second degree polynomial. The concave profiles at the first portion 805 and the third portion 815 can be the same or they can be different (as shown in FIG. 8).

A size of the first portion 805 that includes a certain profile radius (e.g., the first profile radius 818) can be indicated by an angular measurement shown by an angle $\theta_4$ in FIG. 8. A size of the second portion 815 can be a different angular measurement, $\theta_3$, for the second profile radius 820. In some embodiments, the balloon can include multiple different profile radii in the same portion (e.g., in the first portion 805 and/or the second portion 815) and angular measurements can be used to describe the amount of the portion allocated to a particular profile radius and/or the location of that profile radius on the ablation balloon 800.

Figure 9A:
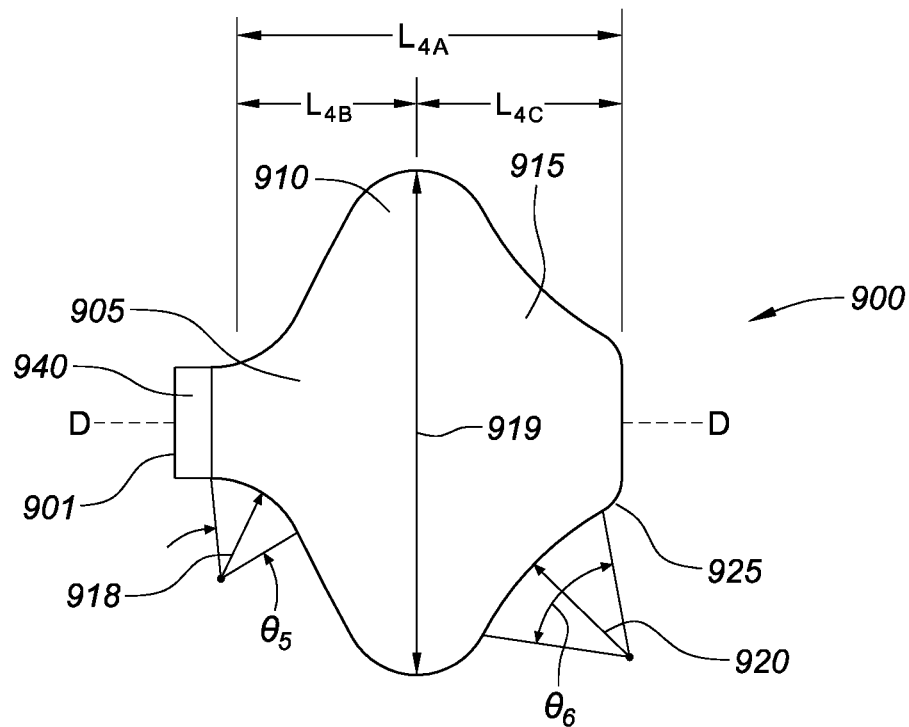
FIG. 9A is a plan view of an ablation balloon, consistent with various aspects of the present disclosure.

FIG. 9A is a plan view of an ablation balloon, consistent with various aspects of the present disclosure. The ablation balloon 900 can have a proximal end 901 with and electrode 940 and a distal end portion 925 and can include a first portion 905 (i.e., a proximal portion; a balloon proximal portion), a second portion 910, and a third portion 915 (i.e., a distal portion; a balloon distal portion). The second portion 910 can include a balloon waist 919 (e.g., a widest diameter of the balloon) that separates the first portion 905 and the third portion 915. The first portion 905 can include a portion of the balloon 900 proximate the proximal end 901. The third portion 915 can have a linear profile (e.g., no radius) or a large radius that results in a nearly linear profile (e.g., a radius larger than second radii profiles 620, 720, and 820 of FIGS. 6-8). The ablation balloon 900 can have a length $L_4$, where the length $L_4$ is from a first location proximate a proximal end 901 to a distal end portion 925 of the ablation balloon 900. The length $L_4$ can range from 10 to 60 mm.

Figure 9B:
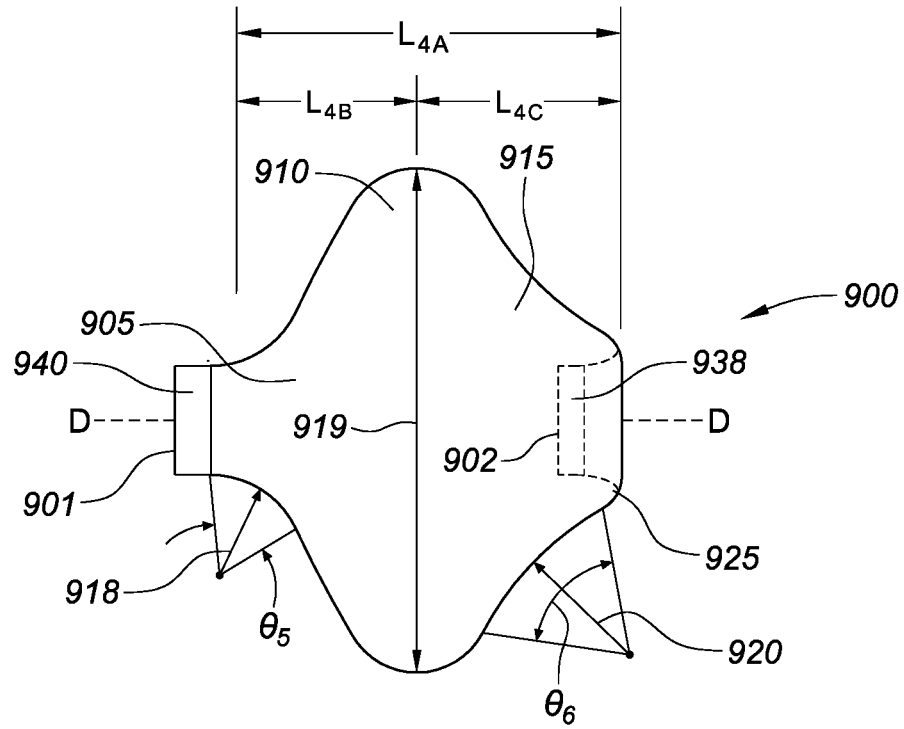
FIG. 9B is a plan view of the ablation balloon of FIG. 9A, consistent with various aspects of the present disclosure.

A distal end portion 925 of the ablation balloon 900 can be formed by, for example, inverting a distal end 902 having an electrode 938 as shown in FIG. 9B, where the distal end 902 of the ablation balloon 900 is moved proximally and faces the opposite direction compared to the distal end portion 925 ablation balloons 600, 700, and 800 shown in FIG. 6-8 (see FIG. 9B for additional information). This configuration can be achieved by, for example, pulling proximally on a shaft (e.g., the shaft 124 of FIG. 1) or other feature that is connected to a distal portion of the ablation balloon 900 and/or pushing distally on a portion of the third portion 915 of the ablation balloon 900, (e.g., with a pull/activation wire connected to a portion of the ablation balloon 900 (not shown) to cause the distal end 902 of the ablation balloon 900 to move towards the proximal end 901 of the ablation balloon 900 (e.g., see FIG. 9B). The configuration in FIG. 9A can, for example, help reduce the risk of undesired perforation of tissue during placement/movement of the ablation balloon 900 compared to the shapes of the ablation balloons 600, 700, and 800 in FIGS. 6-8 due to the blunter profile (e.g., more rounded with fewer protrusions) of the distal end portion 925 of the ablation balloon 900.

The distal end portion 925 of the ablation balloon 900 can also be generated by a pre-formed balloon shape. In this configuration, the balloon 900 is configured to achieve an inflated/expanded shape as shown in FIG. 9A after being deployed.

The ablation balloon 900 can be asymmetrical in shape (e.g., along a longitudinal axis). For example, the ablation balloon 900 can have a first profile radius 918 in the first portion 905 and/or the third portion 915 that is concave and/or linear, The profiles at the first portion 905 and the third portion 915 can be the same or they can be different (as shown in FIGS. 9A and 9B where the profile of the first portion is concave and the profile of the third portion generally linear). Other profiles for the first portion 905 and the third portion 915 are also possible (e.g., linear, convex, combinations of linear/convex/concave, etc.) including combinations of profiles in a single portion (e.g., the first portion 905 can include a linear portion, a first concave portion, and a second concave portion where each concave portion has a different radius, etc.). The shapes of the proximal portion 905 and the distal portion 915 can be described as polynomial expressions, where the polynomial expressions can be at least a second degree polynomial.

A size of the first portion 905 that includes a certain profile radius (e.g., the first profile radius 918) can be indicated by an angular measurement shown by an angle $\theta_5$ in FIG. 9. A size of the second portion 915 can be a different angular measurement, $\theta_6$, for the second profile radius 920. In some embodiments, the balloon can include multiple different profile radii in the same portion (e.g., in the first portion 905 and/or the second portion 915) and angular measurements can be used to describe the amount of the portion allocated to a particular profile radius and/or the location of that profile radius on the ablation balloon 900.

FIG. 9B is a plan view of the ablation balloon of FIG. 9A, consistent with various aspects of the present disclosure. As shown in FIG. 9B, the distal end 902 of the ablation balloon 900 can be inverted (e.g., the distal end 902 of the ablation balloon 900 is facing the proximal end 901) where the distal end 902 of the ablation balloon 900 is pointed towards the proximal end 901, causing the ablation balloon 900 to have a the configuration shown in FIGS. 9A-9B. As described above, the configuration shown in FIG. 9B can be achieved by, for example, pulling proximally on a shaft (e.g., the shaft 124 of FIG. 1) that is connected to a distal portion of the ablation balloon 900 and/or pushing distally on a distal portion of the third portion 915 of the ablation balloon 900, (e.g., with a pull/activation wire connected to a portion of the ablation balloon 900 (not shown) to cause the distal end 902 to move towards the proximal end 901. As described above, the configuration of balloon 900 can also be achieved by the inflated/expanded shape of the balloon.

In various embodiments of the present disclosure, an ablation balloon may include one or more (internal) balloons that may be independently inflated. In one exemplary embodiment, a first (internal) balloon positioned at a proximal end of the ablation balloon may be expanded to deliver ablation therapy circumferentially to the pulmonary vein antrum, and a second (internal) balloon positioned at a distal end of the ablation balloon may be expanded to deliver ablation therapy circumferentially to the pulmonary vein ostia. Such (internal) balloons can relate to portions of the ablation balloons in FIGS. 6 and 7 (e.g., first portions 605 and 705, second portions 610 and 710, and third portions 615 and 715). In one specific embodiment, the one or more internal balloons may be encompassed by an external balloon.

One important benefit of the present disclosure is that ablation balloons, consistent herewith, are associated with decreased esophageal and phrenic nerve interaction with the pulmonary vein. Often times, such interaction is caused by wall distortion due to expansion of the balloon and advancement toward the pulmonary vein. Preventing interaction between the pulmonary veins and the esophageal and phrenic nerves greatly decreases complications related to nerve damage from the ablation therapy.

Various embodiments of the present disclosure are directed to pulmonary vein isolation balloon designs for optimum therapy delivery. Specifically, the balloon designs disclosed herein may be configured to facilitate improved energy delivery or extraction by better alignment between the balloon and the antral and/or proximal ostia portions of the pulmonary vein. The various embodiments disclosed herein may be applied to any of the various balloon-based energy delivery means (such as those discussed in more detail above).

Many cardiac catheter applications utilize the fossa ovalis to enter the heart. Due to the geometry between the fossa ovalis and an entrance to the pulmonary veins in the left atrium, the catheter shaft will naturally be biased towards a left side of the patient, putting pull/torque on the cardiac catheter as it locates (and is positioned in contact with) the pulmonary vein (e.g., for pulmonary vein isolation ablation therapy procedures). This biasing force pulls the catheter shaft off the natural centerline of the pulmonary vein being targeted, causing a variation in the forces and contact surface area experienced between the balloon and the pulmonary vein walls. As an example, when the biasing force pulls an ablation balloon off the natural centerline of a target pulmonary vein, the contact surface area and force exerted by the balloon on the side of the pulmonary vein which receives the additional biasing force will be greater than the other side(s) of the balloon. As a result, the energy delivery or extraction of the catheter is tied to catheter position, and may be one contributor to therapy variation.

Various embodiments of the present disclosure may be directed to multi-shape balloons for ostial and antral coverage of pulmonary vein geometry (e.g., two or more geometries). Such multi-shape balloons may facilitate centering of the balloon within a pulmonary vein for uniform ablation therapy applications, for example. Also, such multi-shape balloons may enable energy delivery to both antral and ostial portions of the pulmonary vein simultaneously (due to the increased contact area)—thereby targeting linear and circumferential conduction paths. In yet further embodiments, the multi-shape balloons may target energy delivery to distal, mid, or proximal balloon surfaces. The multi-shape balloon may also utilize a distal length of the balloon to contact an ostial portion of the pulmonary vein, facilitating proper centering of the balloon in the pulmonary vein while a proximal length of the balloon in contact with an antrum of the pulmonary vein conducts the ablation therapy.

Additional information about ablation balloons can be found in U.S. application No. 62/432,045, filed on 9 Dec. 2016 and U.S. application No. 62/432,065, filed on 9 Dec. 2016, and are hereby incorporated by reference as if set forth fully herein.

Additional information and examples can be found in U.S. application No. 62/578,352, filed Oct. 27, 2017, U.S. application No. 62/578,201, filed Oct. 27, 2017, U.S. application No. 62/578,320, filed Oct. 27, 2017, and U.S. application No. 62/578,325, filed Oct. 27, 2017, each of which is hereby incorporated by reference as if set forth fully herein.

Aspects of the present disclosure are directed to a medical device balloon apparatus. The apparatus including a distal portion with a first circumference, a proximal portion, and an intermediary portion. The proximal portion has a second circumference which is greater than the first circumference, and the intermediary portion has a varying circumference coupled between the proximal and distal portions of the ablation balloon. The distal portion includes a first circumferentially extending surface and the proximal portion includes a second circumferentially extending surface. Both of the first and second circumferentially extending surfaces extending tangential from a radial line extending off a longitudinal axis of the medical device balloon apparatus.

In one exemplary embodiment of the present disclosure, a system for treating atrial fibrillation is taught. The system including a balloon delivery catheter including proximal and distal ends, and an ablation balloon coupled to the distal end of the balloon delivery catheter. The ablation balloon including distal, proximal, and intermediary portions. The distal portion having a first circumference, and engages with an ostium of a pulmonary vein for aligning a longitudinal axis of the ablation balloon with a second longitudinal axis of the pulmonary vein. The proximal portion has a second circumference which is greater than the first circumference. The intermediary portion is coupled between the proximal and distal portions of the ablation balloon, and has a varying circumference. At least one of the proximal and intermediary portions of the ablation balloon engage with an antrum of the pulmonary vein along an uninterrupted length and circumference, and deliver a uniform ablation therapy to the pulmonary vein antrum.

In another embodiment of the present disclosure, a balloon catheter is disclosed for pulmonary vein isolation. The balloon catheter including a catheter shaft, an ablation balloon, and tissue ablation means. The catheter shaft deploys an ablation balloon into a pulmonary vein, which is coupled to a distal end of the balloon delivery catheter. The ablation balloon deploys from an un-deployed configuration and engages with a tissue wall of the pulmonary vein along an uninterrupted length and circumference of an antrum and ostia of the pulmonary vein. The tissue ablation means, in association with the ablation balloon, delivers a uniform ablation therapy around a circumference of the pulmonary vein antrum engaged by the ablation balloon. The ablation balloon also overcomes a biasing force exerted upon the ablation balloon by the catheter shaft by engaging with the ostia of the pulmonary vein to overcome the biasing force.

Based upon the above discussion and illustrations, those skilled in the art will readily recognize that various modifications and changes may be made to the various embodiments without strictly following the exemplary embodiments and applications illustrated and described herein. For example, a deployed ablation balloon, consistent with aspects of the present disclosure, may consist of a number of varying geometries based on imaging data indicative of the internal dimensions of a patient's targeted pulmonary vein. In such an embodiment, the deployed ablation balloon engages the targeted pulmonary vein along an uninterrupted length and circumference of the ablation balloon to maximize the efficacy of the ablation therapy. Such modifications do not depart from the true spirit and scope of various aspects of the disclosure, including aspects set forth in the claims.

Although several embodiments have been described above with a certain degree of particularity to facilitate an understanding of at least some ways in which the disclosure may be practiced, those skilled in the art could make numerous alterations to the disclosed embodiments without departing from the scope of the present disclosure and the appended claims. It is intended that all matter contained in the above description or shown in the accompanying drawings shall be interpreted as illustrative only and not limiting. Accordingly, the examples and embodiments herein should not be construed as limiting the scope of the disclosure. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements may not have been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

The terms "including," "comprising" and variations thereof, as used in this disclosure, mean "including, but not limited to," unless expressly specified otherwise. The terms "a," "an," and "the," as used in this disclosure, means "one or more," unless expressly specified otherwise.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation.

Although process steps, method steps, algorithms, or the like, may be described in a sequential order, such processes, methods, and algorithms may be configured to work in alternative orders. In other words, any sequence or order of steps that may be described does not necessarily indicate a requirement that the steps be performed in that order. The steps of the processes, methods, and algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. However, surgical instruments may be used in many orientations and positions, and these terms are not intended to be limiting and absolute. All other directional or spatial references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An elongate medical device having a device longitudinal axis and a device distal region, the elongate medical device comprising:
 a balloon at the device distal region and having a balloon longitudinal axis, the balloon comprising:
  a balloon proximal portion;
  a balloon distal portion that is distal of the balloon proximal portion; and a balloon inflatable portion with a first length that is configured to transition from a deflated state to an inflated state, wherein the balloon inflatable portion includes a portion of the balloon proximal portion and a portion of the balloon distal portion, and wherein, in the inflated state, the balloon is symmetrical about the balloon longitudinal axis;

wherein the balloon proximal portion has a second length and a first profile shape, the first profile shape including a first concave shape with a first profile radius; and wherein the balloon distal portion has a third length and a second profile shape, the second profile shape including a i) second concave shape with a second profile radius greater than the first profile radius and ii) a substantially concave tissue contacting surface, and wherein the second length of the balloon proximal portion is less than the third length of the balloon distal portion.

2. The elongate medical device of claim 1, wherein the first profile shape and the second profile shape are each defined by a polynomial expression, wherein the polynomial expression is at least a second degree polynomial.

3. The elongate medical device of claim 1, wherein the second profile shape is defined by one or more curves.

4. The elongate medical device of claim 3, wherein the first profile shape is defined by one or more curves.

5. The elongate medical device of claim 1, wherein the first profile shape is defined by a linear portion in between two curved portions and the second profile shape is defined by a linear portion in between two curved portions.

6. The elongate medical device of claim 1, wherein the second profile shape is further defined by a first angle.

7. The elongate medical device of claim 1, wherein the first profile shape is further defined by a second angle.

8. The elongate medical device of claim 1, wherein the first concave shape and the second concave shape comprise unequal concave shapes.

9. The elongate medical device of claim 1, wherein the proximal portion comprises a plurality of profile shapes.

10. The elongate medical device of claim 1, wherein the first length is between 10 and 60 mm.

11. The elongate medical device of claim 1, wherein the second profile radius is between 1 and 5 mm.

12. The elongate medical device of claim 1, wherein the balloon distal portion includes an inverted portion that extends from a distal end of the balloon distal portion back towards the balloon proximal portion along a portion of the remainder of the balloon distal portion.

13. A system for treating atrial fibrillation, the system comprising:
a balloon delivery catheter including a proximal end and a distal end; and
an ablation balloon having a first length, the ablation balloon comprising a first section, a second section, a third section, and an inflatable section that comprises the second section and portions of the first and third sections, wherein the ablation balloon is coupled to the distal end of the balloon delivery catheter, and wherein:
the first section has a first profile shape and a second length, the first profile shape including a first concave shape with a first profile radius;
the third section has a second profile shape and a third length, the second profile shape including i) a second concave shape with a second profile radius greater than the first profile radius and ii) a substantially concave tissue contacting surface, wherein the second length of the first profile shape is less than the third length of the second profile shape,
a portion of the third section is configured to engage with an ostium of a pulmonary vein for aligning a longitudinal axis of the ablation balloon with a longitudinal axis of the pulmonary vein,
the second section is coupled between the first and third sections of the ablation balloon, and
at least a portion of one of the second section and third section of the ablation balloon is configured, when the inflatable section is inflated, to engage with an antrum of the pulmonary vein along an uninterrupted length and circumference, and deliver a uniform ablation therapy to the pulmonary vein antrum.

14. The system of claim 13, wherein the ablation balloon is configured to deliver a consistent ablation therapy delivery along the uninterrupted length and circumference of the pulmonary vein antrum.

15. The system of claim 14, wherein the first concave shape and the second concave shape comprise unequal concave shapes.

16. The system of claim 14, wherein the ablation balloon has a longitudinal length between 10 and 60 mm.

17. The system of claim 14, wherein the ablation balloon ablates tissue using one or more of cryogenic fluid ablation, laser energy, radiofrequency energy, microwave energy, irreversible electroporation, chemical reaction, and high-intensity focused ultrasound.

18. A balloon catheter for pulmonary vein isolation comprising:
a catheter shaft configured to deploy an ablation balloon into a pulmonary vein; and
the ablation balloon coupled to a distal end of the catheter shaft, the ablation balloon comprising a balloon proximal portion and a balloon distal portion that is distal of the balloon proximal portion, wherein the proximal portion of the ablation balloon has a first profile shape, the first profile shape including a first concave shape with a first profile radius,
wherein the distal portion of the ablation balloon has a second profile shape, the second profile shape including i) a second concave shape with a second profile radius greater than the first profile radius and ii) a substantially concave tissue contacting surface, and wherein a length of the balloon proximal portion is less than a length of the balloon distal portion,
wherein the ablation balloon is configured to:
deploy from an undeployed configuration to a deployed configuration, and
engage, by the substantially concave tissue contacting surface, a tissue wall of the pulmonary vein along an uninterrupted length and circumference of an antrum and ostia of the pulmonary vein,
wherein the ablation balloon is configured to deliver a uniform ablation therapy to the antrum of the pulmonary vein engaged by the substantially concave tissue contacting surface of the ablation balloon.

19. The balloon catheter of claim 18, wherein the uniform ablation therapy comprises one or more of the following: cryoablation, laser energy, radiofrequency energy, microwave energy, irreversible electroporation, chemical reaction, and high-intensity focused ultrasound.

20. The balloon catheter of claim 18, wherein the ablation balloon includes a central balloon portion coupled between the balloon proximal portion and the balloon distal portion, the central balloon portion having a varying circumference; and wherein the central portion is configured to engage with an ostia of a pulmonary vein.

21. The balloon catheter of claim 20, wherein the first profile shape and the second profile shape comprise unequal concave shapes.

22. The balloon catheter of claim 20, wherein the ablation balloon has a longitudinal length between 10 and 60 mm.

23. An expandable medical device comprising:
a balloon that is configured to transition from a deflated state to an inflated state, the balloon comprising a balloon proximal portion and a balloon distal portion that is distal of the balloon proximal portion, wherein when the balloon is in the inflated state, the balloon proximal portion has a first profile shape and the balloon distal portion has a second profile shape,
wherein the first profile shape includes a first concave shape with a first profile radius,
wherein the second profile shape includes a i) second concave shape with a second profile radius greater than the first profile radius and ii) a substantially concave tissue contacting surface, wherein the balloon is configured to be coupled with an elongated medical device, and wherein a length of the balloon proximal portion is less than a length of the balloon distal portion.

* * * * *